US00PP34898P2

(12) United States Plant Patent
Gruber

(10) Patent No.: US PP34,898 P2
(45) Date of Patent: Jan. 3, 2023

(54) ***HEUCHERA* PLANT NAMED 'GRATEFUL GATHERING'**

(50) Latin Name: *Heuchera villosa*
Varietal Denomination: Grateful Gathering

(71) Applicant: Wayne A Gruber, Crown Point, IN (US)

(72) Inventor: Wayne A Gruber, Crown Point, IN (US)

( * ) Notice: Subject to any disclaimer, the term of this patent is extended or adjusted under 35 U.S.C. 154(b) by 0 days.

(21) Appl. No.: 17/803,539

(22) Filed: Aug. 17, 2022

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
See application file for complete search history.

*Primary Examiner* — Annette H Para

(57) ABSTRACT

The new *Heuchera* plant named 'Grateful Gathering' has medium-sized, shallowly-dissected, palmate leaves with cordate bases. The leaves are chartreuse when young and develop to light gold to chartreuse in color. The small campanulate flowers have white reflexed petals displayed on stiff, erect, tightly branched stems. The new plant has a vigorous growth and sturdy plant habit and is useful in the garden landscape or in containers.

5 Drawing Sheets

Botanical classification: *Heuchera villosa.*
Cultivar designation: 'Grateful Gathering'.

BACKGROUND OF THE INVENTION

The present invention relates to a new and distinct cultivar of Coral Bells plant of hybrid origin, botanically known as *Heuchera* 'Grateful Gathering' and is hereinafter referred to by its cultivar name 'Grateful Gathering'.

The new cultivar was discovered as a chance uninduced sport of *Heuchera* 'Caramel' U.S. Plant Pat. No. 16,560 in a nursery garden by the Inventor in Lowell, Ind. in the late spring of 2006. The sport was observed for many years, propagated and tested for uniformity and observed for several more years. The new plant has not been sold anywhere in the world nor disclosed to the public in any way.

Asexual propagation of the new cultivar was first accomplished under the direction of the Inventor by crown division initiated in the fall of 2006 in Lowell, Ind. Examination of asexually propagated plants of 'Grateful Gathering' has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Grateful Gathering' as a new and distinct cultivar of *Heuchera:*

1. Medium-sized, shallowly-dissected, palmate foliage with cordate base;
2. Foliage that is variably light gold to chartreuse in color;
3. Erect, stiff, tightly branched flower stems;
4. Small campanulate flowers with white reflexed petals;
5. Exhibits vigorous growth with sturdy plant habit;

'Grateful Gathering' can be most closely compared to the *Heuchera* cultivars: 'Amber Waves' (U.S. Plant Pat. No. 13,348), 'TNHEUCHA' (U.S. Plant Pat. No. 27,567), 'Toffee Tart' (U.S. Plant Pat. No. 33,694) and 'Ginger Ale' (U.S. Plant Pat. No. 18,173).

'Amber Waves' has foliage that is more dissected, more ruffled, and orangish-colored, with peduncles that are more reddish-orange. 'TNHEUCHA' (more commonly known as 'Champagne') has more peachy-colored foliage and the peduncles and pedicels are more greyed-red. 'Toffee Tart' has foliage that is more ginger-colored. 'Ginger Ale' differs from 'Grateful Gathering' in having foliage that is smaller in size, more dissected, more cinnamon-colored with lighter cream between the veins early in the season, the flowers are more chartreuse, and the peduncles and pedicels are more reddish.

'Caramel' has foliage that emerges greyed-orange-colored and develops to golden chartreuse, and the peduncles are more greyed-reddish-colored.

BRIEF DESCRIPTION OF THE DRAWINGS

The accompanying color photographs illustrate the overall appearance and distinct characteristics of the new *Heuchera*. The photographs were taken of two-year-old plants grown outdoors in a trial garden and in containers in a partially shaded greenhouse in Lowell, Ind. with the flower photographs taken of a three-year-old plant grown in a trial garden in Zeeland, Mich. The colors in the photographs are as close as possible given the current digital photography techniques available. The color values cited in the detailed botanical description accurately describe the colors of the new *Heuchera.*

The photograph in FIG. 1 provides a side view of the plant of 'Grateful Gathering' prior to flowering.

Figure 1:
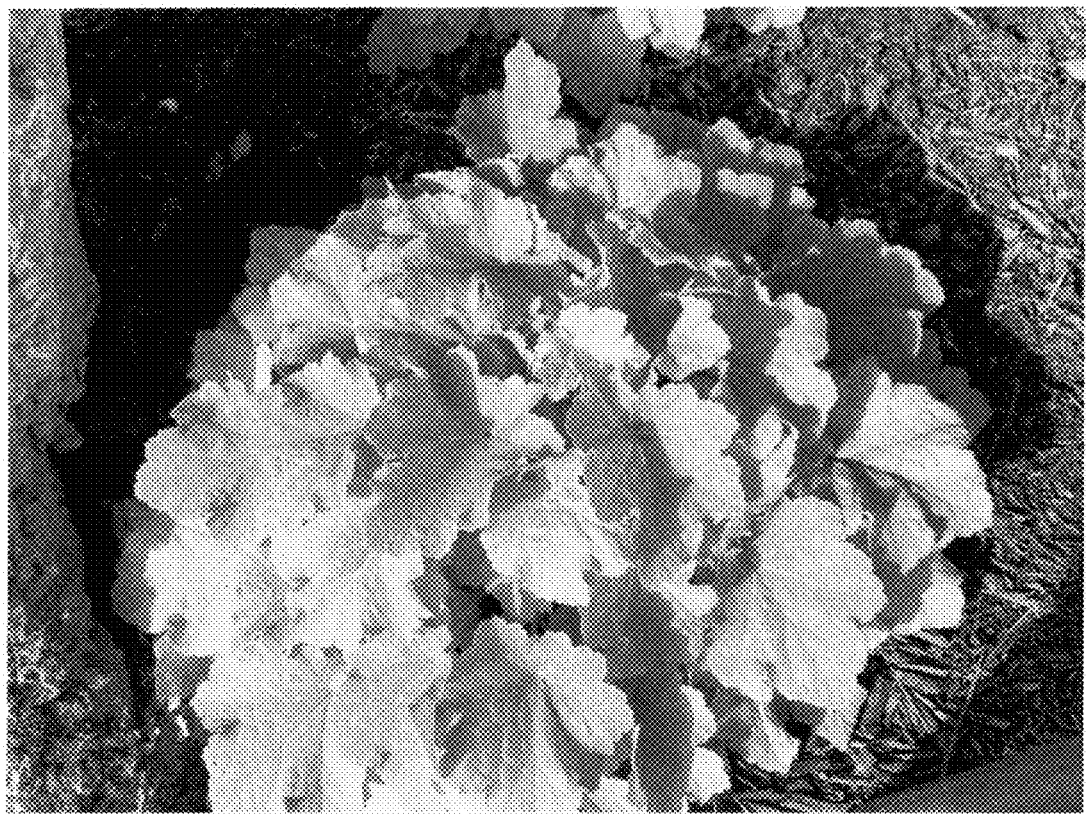
Figure 2:
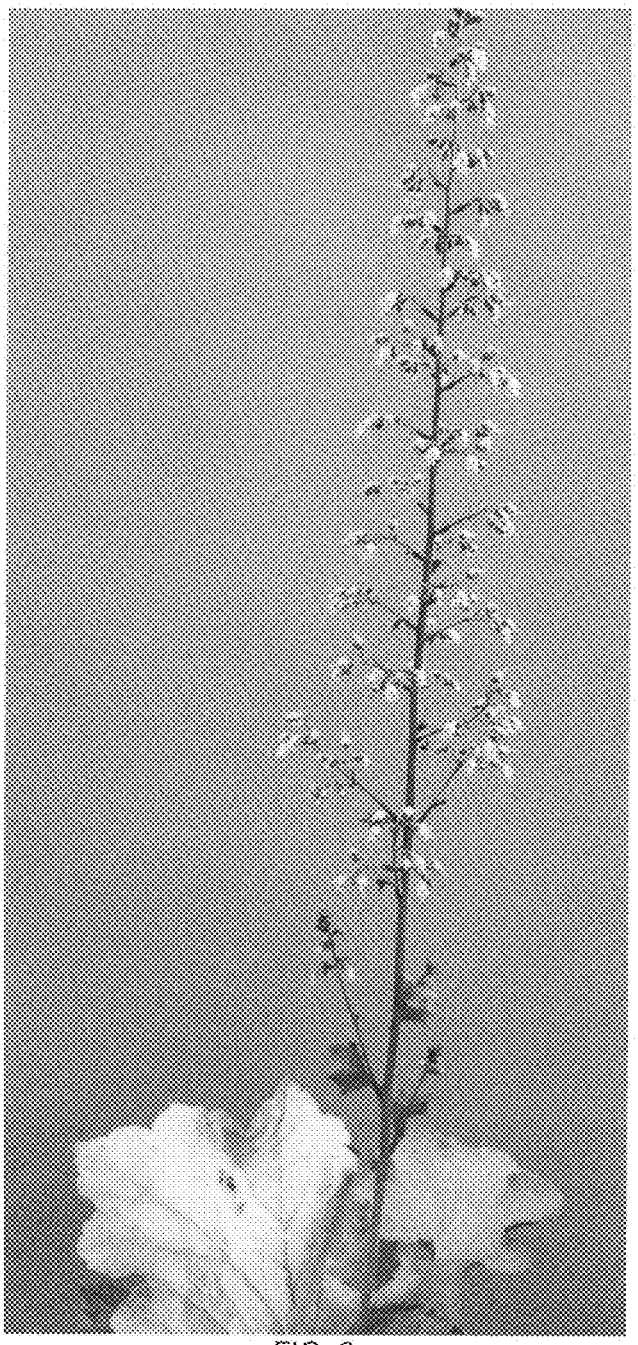

The photograph in FIG. 2 provides a view of an inflorescence of 'Grateful Gathering'.

Figure 3:
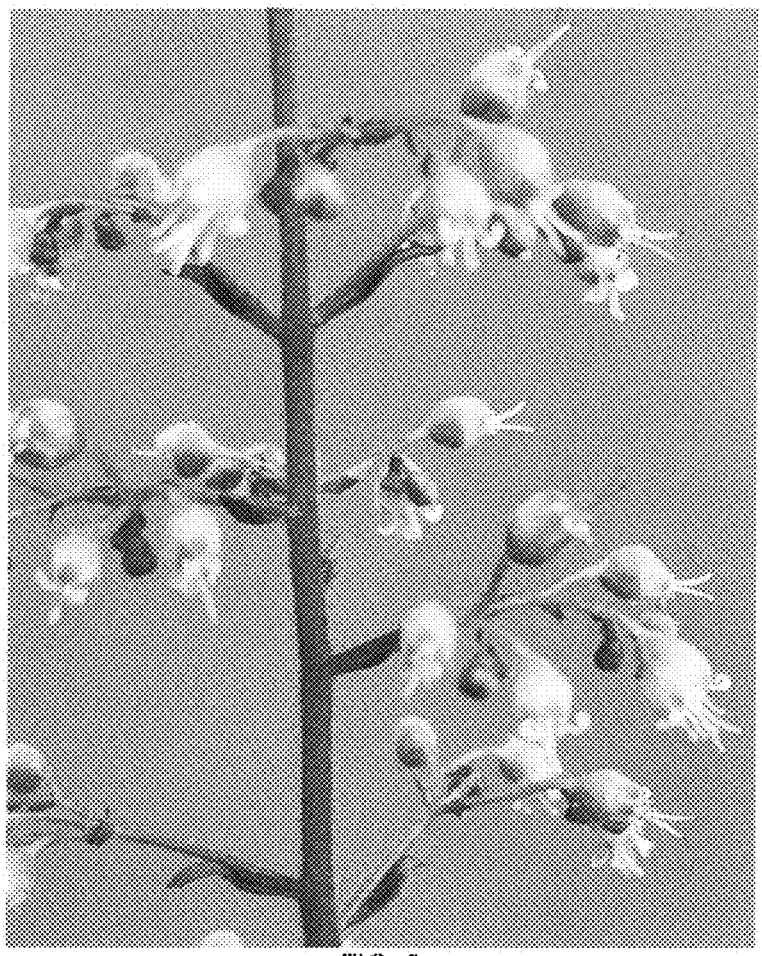

The photograph in FIG. 3 provides a close-up of the middle branches of the stem showing flowers and buds.

Figure 4:
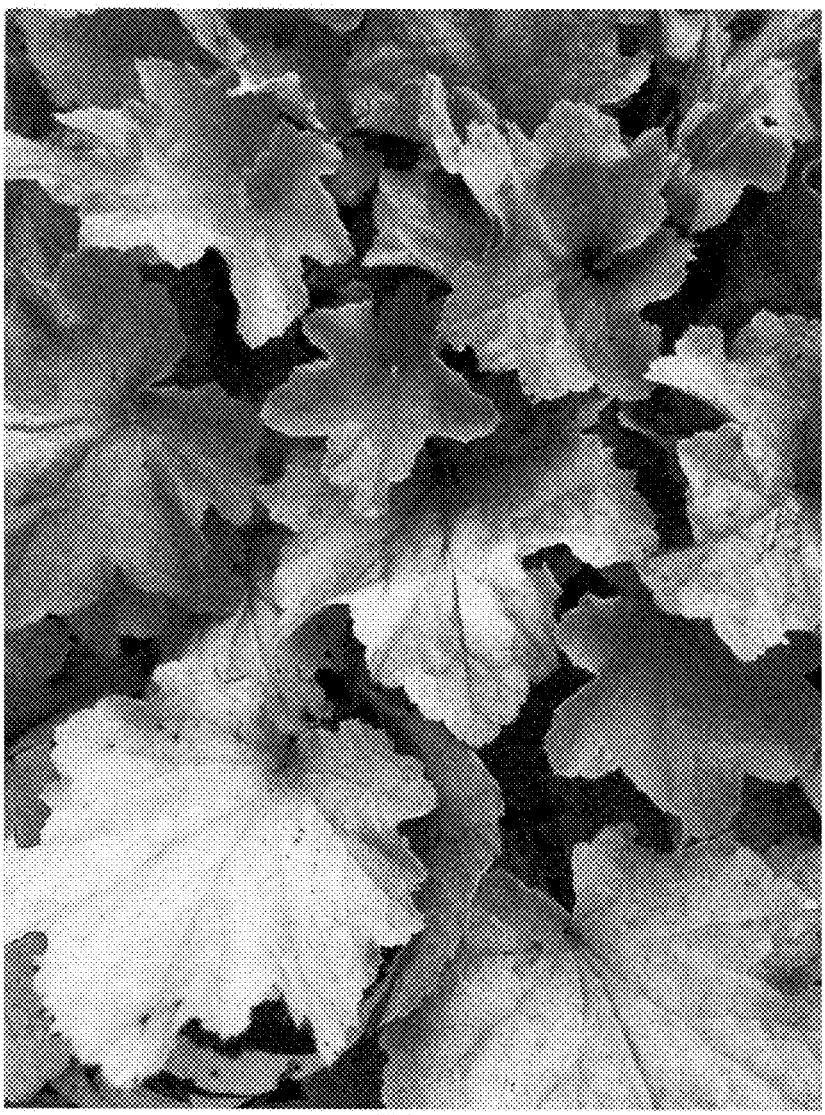

The photograph in FIG. 4 provides a close-up view of the foliage of 'Grateful Gathering' at flowering.

Figure 5:
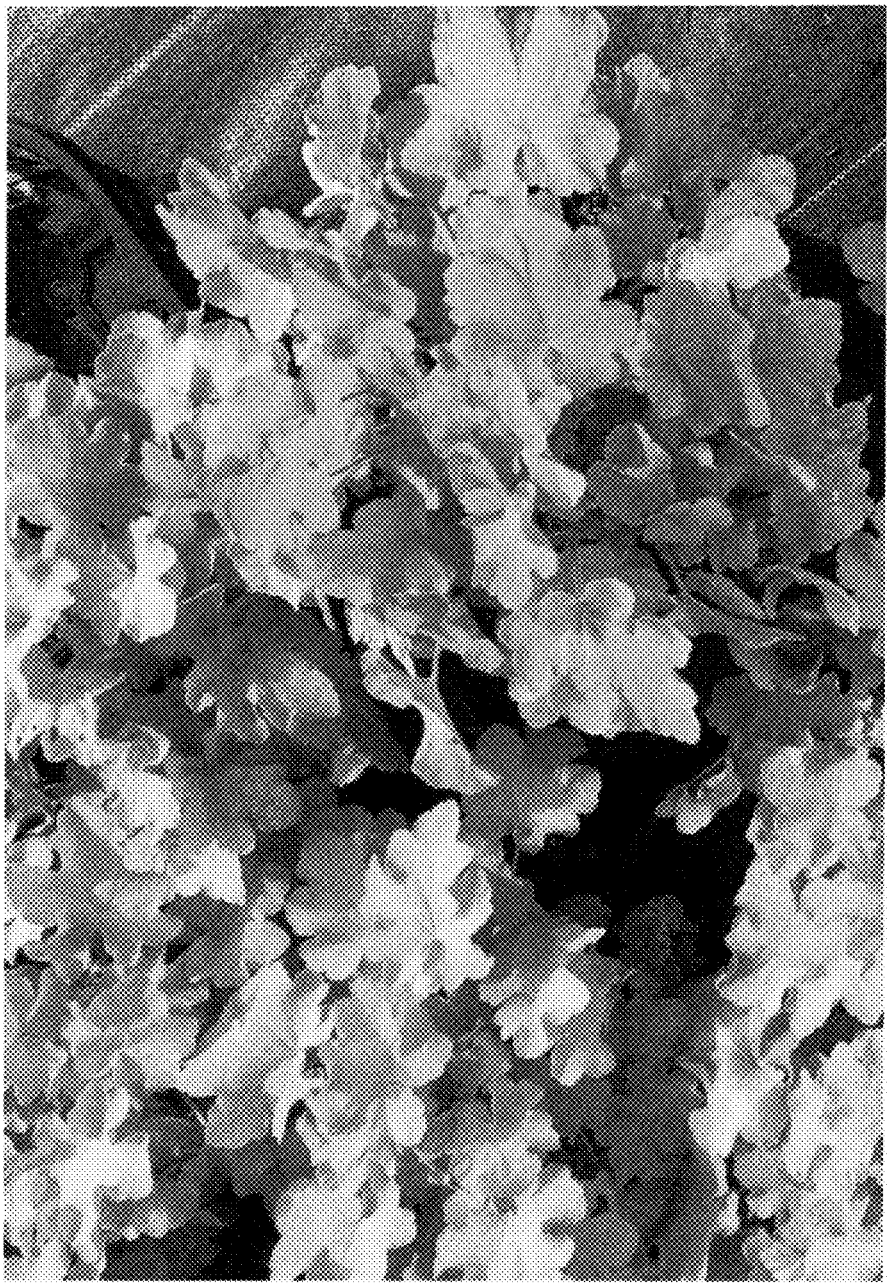

The photograph in FIG. 5 provides a comparison of 'Caramel' (top) and 'Grateful Gathering' (bottom).

DETAILED BOTANICAL DESCRIPTION OF THE PLANT

The following is a detailed description of three-year-old plants of the new cultivar as grown outdoors in a partially shaded trial garden in Zeeland, Mich. and Lowell, Ind. The phenotype of the new cultivar may vary with variations in environmental, climatic, and cultural conditions, as it has not been tested under all possible environmental conditions. The color determination is in accordance with "The 2015 Colour Chart" of The Royal Horticultural Society, London, England, except where general color terms of ordinary dictionary significance are used.

General description:

*Blooming period*.—At least 4 weeks in the Upper Midwest of the U.S.

*Plant type*.—Herbaceous perennial.

*Plant habit*.—Broadly rounded mound with inflorescences held above the foliage.

*Height and spread*.—Foliage to about 37 cm tall and flowers to about 65 cm tall and foliage to about 80 cm wide.

*Cold hardiness*.—To at least in U.S.D.A. Zone 3.

*Diseases and pests*.—No susceptibility or resistance to pests or diseases has been observed beyond that normal for *Heuchera*.

*Root description*.—Fibrous roots on semi-woody rootstalks, color nearest 158D.

*Propagation*.—Division and shoot tip tissue culture.

*Root development*.—About 3 weeks for root initiation, 6 weeks to produce a rooted cutting.

*Growth rate*.—Vigorous; filling a 3.8-liter pot in about 2 to 3 months from a 25 mm plug.

*Stem number*.—About 30 basal rosettes.

Foliage description:

*Leaf shape*.—Palmately cordate; slightly concave.

*Leaf division*.—Simple.

*Leaf base*.—Cordate; lobes free.

*Leaf apex*.—Short and abruptly acute.

*Leaf margins*.—Crenate with abruptly acute tips on each tooth, micro-ciliolate; slightly coarsely undulate.

*Leaf venation*.—Palmate; adaxial slightly concaved and sparsely puberulent; abaxial costate and pubescent.

*Vein color*.—Young adaxial primary and secondary veins between RHS 145A and RHS 146D, minute tertiary veins nearest RHS 177C; young abaxial primary and secondary veins nearest RHS 146D, minute tertiary veins 177B; mature adaxial primary veins nearest RHS 145A, secondary and tertiary veins variable nearest RHS 146B and nearest 146D; mature abaxial primary and secondary veins nearest RHS 145B with tertiary veins variable nearest RHS 147B and nearest RHS 152D.

*Leaf attachment*.—Petiolate.

*Leaf arrangement*.—Rosulate.

*Leaf lobes*.—7 to 11 lobes; shallowly lobed, divergent.

*Leaf surface*.—Adaxial surface sparsely puberulent, adaxial puberulent; adaxial hairs about 0.5 mm, abaxial hairs about 1 mm in length and too small to measure color.

*Leaf color*.—Young adaxial nearest RHS 152B; young abaxial between RHS 182A and RHS 183D; mature adaxial variable, nearest RHS 161C, between RHS 160B and RHS 161B and RHS 146C; mature abaxial variable between RHS N186C and RHS 183B, nearest RHS 176B, nearest RHS 182B, and nearest RHS 161B with a slight blush of nearest RHS 183D.

*Leaf size*.—To about 15 cm long and 13.7 cm wide, average about 12 cm long and 12 cm wide.

*Leaf quantity*.—About 8 per stem.

*Petioles*.—Cylindrical; clasping base; pubescent to hirsutulous; to about 23 cm long and 10 mm across at base; strong and stiff.

*Petiole color*.—Nearest RHS 145A.

*Stipules*.—At the base of each petiole, about 18 mm long and 10 mm across at base; acute apices.

*Stipule color*.—Nearest RHS 185D adaxial and abaxial nearest RHS 185D proximally and distally nearest RHS 187D.

Flower description:

*Inflorescence type*.—Panicle with numerous small bell-shaped flowers arranged on panicles on peduncles emerging from a basal rosette.

*Inflorescence size*.—To 65 cm in height and branching to 8 cm wide.

*Inflorescence number*.—About 11.

*Density of flowers per inflorescence*.—Medium.

*Flower fragrance*.—None observed.

*Flower quantity*.—Up to 470 flowers per peduncle, average of 350 flowers with about 3,500 per plant.

*Flower lastingness*.—About 4 to 6 days.

*Flower buds*.—Obovate with acute apex and attenuate base; micro-puberulent; about 3 mm long and 2.5 mm diameter.

*Flower bud color*.—Nearest RHS 146B with light blush dorsally nearest RHS 183C.

*Flower aspect*.—Slightly drooping about 45° below horizontal.

*Flower type*.—Single; campanulate; perfect; complete.

*Flower size*.—About 6 mm long to exserted anthers and 4 mm across.

*Petals*.—Typically 5; rotate; oblanceolate; margin entire; apex acute and reflexed; base narrowly attenuate; glabrous, smooth, and matte adaxial and abaxial; about 3 mm long and 0.7 mm wide near apex.

*Petal color*.—When first opening and fully opened adaxial and abaxial nearest RHS NN155D.

*Calyx*.—Campanulate, sepals fused to hypanthium, 3.5 mm long and 3 mm across.

*Sepals*.—Typically 5; about 3 mm long and 1 mm across at fusion, proximal 2 mm fused into hypanthium; ovate; rounded apex; entire margin.

*Sepal color*.—When first opening and fully opened adaxial and abaxial apical 0.5 mm nearest RHS 146B, fused hypanthium abaxial nearest RHS 146C, adaxial and abaxial between apex and fused hypanthium nearest RHS NN155C with a faint blush of nearest RHS 183B.

*Peduncle*.—Cylindrical; erect; heavily branched with about 35 branches; pubescent to hirsutulous with hairs about 1 mm long; to 65 cm in length and 4 mm in diameter.

*Peduncle color*.—Proximally between RHS 145A and RHS 146D, distally between RHS 146B and RHS 146C; hairs tinted nearest RHS 183B.

*Branches*.—Extending at about a 45° angle from main stem, greater distally and less proximally; cylindrical; puberulent; to about 7 cm long and 1 mm diameter.

*Branch color*.—Between RHS 146B and RHS 146C; hairs tinted nearest RHS 183B.

*Pedicels*.—Cylindrical; micro-puberulent, matte; to about 3 mm long and 0.5 mm diameter; moderate strength.

*Gynoecium*.—Single, split.

*Pistil*.—Split in two, 5.5 mm long.

*Ovary*.—Conical; glabrous; lustrous; truncate base and acute apex tapering to style; 2 mm long and 1.5 mm across; color nearest RHS 145C.

*Style*.—Cylindrical; lustrous; glabrous; about 3 mm long, 0.5 mm across at base, tapering to stigma; split in two above ovary; color nearest RHS NN155B.

*Stigma*.—Minute; globose; about 0.1 mm diameter; color nearest 196D.

*Androecium*.—Five.

*Anthers*.—Five; ellipsoidal; about 0.5 mm long and 0.3 mm wide; color nearest RHS 4D.

*Filament*.—Cylindrical; lustrous; about 2.5 mm long and 0.1 mm diameter; color nearest RHS NN155D.

*Pollen*.—Not observed.

*Fruit and seed*.—Not observed to date.

I claim:

1. The new and distinct *Heuchera* plant named 'Grateful Gathering' as herein described and disclosed.

* * * * *